US012647745B2

(12) United States Patent
Shen

(10) Patent No.: US 12,647,745 B2
(45) Date of Patent: Jun. 2, 2026

(54) INFORMATION PROCESSING APPARATUS, INFORMATION PROCESSING METHOD, AND COMPUTER-READABLE STORAGE MEDIUM

(71) Applicants:Sony (China) Limited, Beijing (CN); Sony Group Corporation, Tokyo (JP)

(72) Inventor: Linghao Shen, Beijing (CN)

(73) Assignees: SONY (CHINA) LIMITED, Beijing (CN); SONY GROUP CORPORATION, Tokyo (JP)

( * ) Notice: Subject to any disclaimer, the term of this patent is extended or adjusted under 35 U.S.C. 154(b) by 223 days.

(21) Appl. No.: 18/411,099

(22) Filed: Jan. 12, 2024

(65) Prior Publication Data

US 2024/0251218 A1     Jul. 25, 2024

(30) Foreign Application Priority Data

Jan. 20, 2023    (CN) .......................... 202310050843.1

(51) Int. Cl.
*H04S 7/00*        (2006.01)
*A61B 5/107*       (2006.01)
(52) U.S. Cl.
CPC ............... *H04S 7/303* (2013.01); *H04S 7/40* (2013.01); *A61B 5/107* (2013.01); *H04S 2400/11* (2013.01); *H04S 2400/15* (2013.01)

(58) Field of Classification Search
CPC . H04S 7/303; H04S 7/40; H04S 7/302; H04S 2400/11
USPC .................................. 381/303–305, 309–310
See application file for complete search history.

(56)                References Cited

U.S. PATENT DOCUMENTS

2012/0269332 A1*  10/2012  Mukund ................. H04S 3/006
                                                            704/201
2021/0195360 A1*   6/2021  Leider ................... A63F 13/577

* cited by examiner

*Primary Examiner* — George C Monikang
(74) *Attorney, Agent, or Firm* — XSENSUS LLP

(57)              ABSTRACT

The present disclosure relates to an information processing apparatus, an information processing method, and a computer-readable storage medium. The information processing apparatus according to the present disclosure includes processing circuitry configured to: obtain a sound field in a virtual space, by using a sound field synthesis model, based on sound source information about a sound source in a real space and virtual space information indicating an object present in a virtual space. The sound field synthesis model is pre-obtained through machine learning by using a sound field in a virtual space obtained from high-precision calculation as learning data.

16 Claims, 11 Drawing Sheets

220

222

(a)

(b)

(c)

INFORMATION PROCESSING APPARATUS, INFORMATION PROCESSING METHOD, AND COMPUTER-READABLE STORAGE MEDIUM

CROSS-REFERENCE TO RELATED APPLICATION

The present application claims priority to Chinese Patent Application No. 202310050843.1, filed on Jan. 20, 2023, the content of which is incorporated herein by reference in its entirety.

FIELD

The present disclosure relates to the field of information processing, and more particularly, to an information processing apparatus, an information processing method, and a computer-readable storage medium, which are conducive to providing a virtual space sound field with a high degree of reality in real time.

BACKGROUND

With the development of virtual reality technology, how to provide users with various real experiences, such as a real sound experience, in a virtual space such as the Metaverse has attracted increasing attention.

Generally, a highly realistic sound field may be generated through a complex simulation algorithm from complex information. However, a high-precision simulation requires a large amount of calculation, and therefore has a low real-time performance. Simply calculating the sound field by using an ideal model may meet the requirement of the real-time performance, but the obtained sound field has a low degree of reality.

Therefore, it is desired to provide a method for generating a virtual space sound field which can simultaneously meet requirements of a degree of reality and real-time performance

SUMMARY

Hereinafter provided is a brief summary of the present disclosure, which is intended to provide a basic understanding of aspects of the present disclosure. It should be understood, however, that this summary is not an exhaustive overview of the present disclosure. The summary is not intended to identify key or critical portions of the present disclosure or to delineate the scope of the disclosure. The purpose is merely to present some concepts about the present disclosure in a simplified form, as a prelude to the more detailed description that is presented later.

An objective of embodiments of the present disclosure is to provide an information processing apparatus, an information processing method, and a computer-readable storage medium, with which a sound field in a virtual space such as the Metaverse can be provided with a high degree of reality in real time.

According to an aspect of the present disclosure, an information processing apparatus is provided. The information processing apparatus includes processing circuitry configured to: obtain a sound field in a virtual space, by using a sound field synthesis model, based on sound source information about a sound source in a real space and virtual space information indicating an object present in the virtual space, where the sound field synthesis model is pre-obtained through machine learning by using a sound field in a virtual space obtained from high-precision calculation as learning data.

According to another aspect of the present disclosure, an information processing method is provided. The information processing method includes: obtaining a sound field in a virtual space, by using a sound field synthesis model, based on sound source information about a sound source in a real space and virtual space information indicating an object present in the virtual space, where the sound field synthesis model is pre-obtained through machine learning by using a sound field in a virtual space obtained from high-precision calculation as learning data.

According to yet another aspect of the present disclosure, a non-transitory computer-readable storage medium storing executable instructions is provided. The executable instructions, when executed by a processor, cause the processor to perform the information processing method or functions of the information processing apparatus.

According to other aspects of the present disclosure, computer program codes and a computer program product for implementing the above-mentioned method according to the present disclosure are further provided.

According to at least one aspect of embodiments of the present disclosure, the virtual space sound field can be obtained based on the sound source information and the virtual space information, by using the sound field synthesis model pre-obtained from high-precision learning data. Thereby, with the real-time, high-precision computing capability of the pre-trained sound field synthesis model (i.e., a result of a fast approximation of high-precision simulation), the sound field in the virtual space, such as the Metaverse, is provided with a high degree of reality in real time.

Other aspects of the embodiments of the present disclosure are set forth in the following sections of the specification, where the detailed description is provided to fully disclose preferred embodiments of the embodiments of the present disclosure, rather than to impose limitations thereon.

BRIEF DESCRIPTION OF THE DRAWINGS

The accompanying drawings described herein are only for illustrative purposes of selected embodiments, rather than all possible embodiments, and are not intended to limit the scope of the present disclosure. In the accompanying drawings.

Figure 1A:
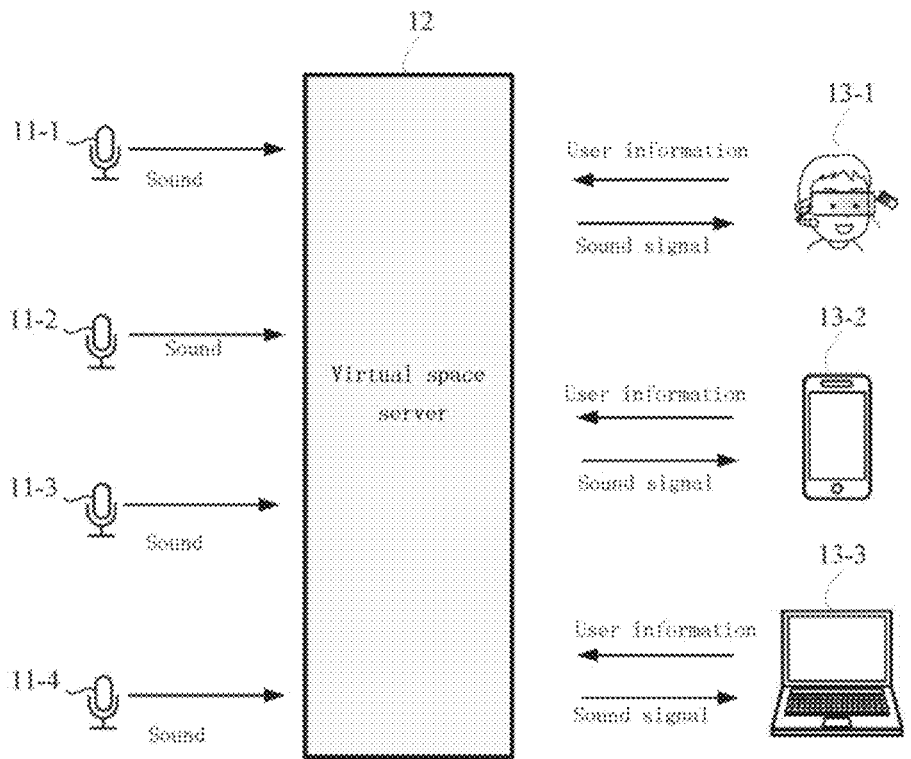
FIG. 1A and FIG. 1B are schematic diagrams for illustrating examples of an information processing system to which the technology of the present disclosure can be applied.

Although the present disclosure is easily subjected to various modifications and replacements, specific embodiments thereof, as examples, are shown in the drawings and described in detail here. However, it should be understood that, the description of specific embodiments herein is not intended to limit the present disclosure to specific forms that are disclosed. On the contrary, an object of the present disclosure is to cover all modifications, equivalents and replacements that fall within the spirit and scope of the present disclosure. It should be noted that throughout the several drawings, corresponding components are indicated by corresponding reference numerals.

DETAILED DESCRIPTION

Examples of the present disclosure are now fully described with reference to the accompanying drawings. The following description is merely substantially exemplary and is not intended to limit the present disclosure, an application or use thereof.

Exemplary embodiments are provided so that the present disclosure is described in detail and fully conveys the scope thereof to those skilled in the art. Examples of specific components, apparatus, methods and other specific details are set forth to provide detailed understanding of embodiments of the present disclosure. It will be apparent to those skilled in the art that the exemplary embodiments may be implemented in many different forms without the use of specific details, and they should not be construed as limiting the scope of the present disclosure. In some exemplary embodiments, well-known processes, well-known structures, and well-known technologies are not described in detail.

The description is given in the following order.
1. Overview
2. Exemplary configuration of an information processing apparatus
2.1 Example of a basic configuration
2.2 Exemplary configuration of a sound field generation unit
2.3 Exemplary configuration of a sound signal generation unit
2.4 Exemplary application scenario
3. Method embodiment
4. Application example

1. Overview

As mentioned above, it is expected to provide a method suitable for generating a sound field in a virtual space (that is also referred to as a virtual space sound field in this specification).

A conventional solution is to perform a simulation based on complex information such as sound source information, obstacle attributes and the like by using a probabilistic model, through a method such as Monte Carlo integration. Although this method may provide a result with a high degree of reality, the high-precision simulation requires a large amount of calculation and takes a long time, which results in a low real-time performance.

Another conventional solution is to calculate geometric and scattering attenuation of sound signals from sound sources based on an ideal model by using simple information such as sound source information, obstacle positions and the like, and superimpose the attenuated sound signals. Although this method is relatively simple to calculate and helps improving a processing speed, the result provided by the method has a low degree of reality.

In view of the above problems, the present disclosure proposes a concept in which a sound field synthesis model is pre-obtained through machine learning by using, as learning data, a sound field in a virtual space that is obtained from high-precision calculation. Then, a sound field in a virtual space is obtained by using the sound field synthesis model based on sound source information about a sound source in a real space and virtual space information indicating an object present in the virtual space. In this way, requirements of precision and real-time performance are satisfied.

Based on the above concept, an information processing apparatus, an information processing method, and a computer-readable storage medium are provided according to embodiments of the present disclosure.

Figure 1B:
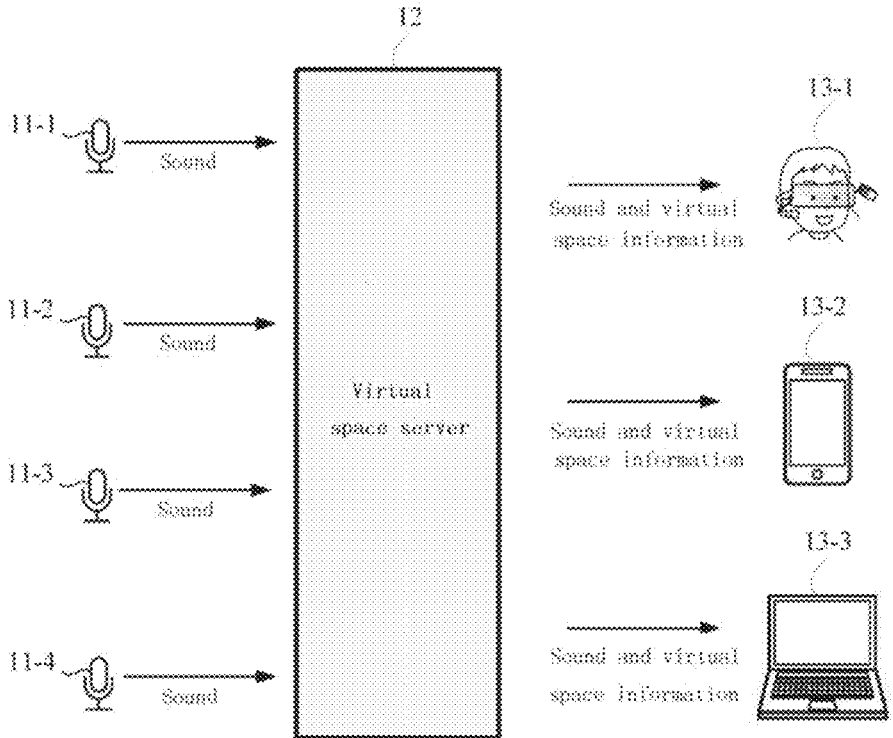

FIG. 1A and FIG. 1B are schematic diagrams for illustrating examples of an information processing system to which the technology of the present disclosure can be applied. As shown in FIG. 1A, an information processing system to which the technology of the present disclosure can be applied may include: sound collection apparatuses 11-1 to 11-4 (which are collectively referred to as a sound collection apparatus 11 when it is unnecessary to distinguish therebetween), such as microphones, a virtual space server 12 for providing a virtual space service as an example of an information processing apparatus according to an embodiment, terminal devices 13-1 to 13-3 (which are collectively referred to as a terminal device 13 when it is unnecessary to distinguish therebetween), such as a head-mounted display, a mobile phone, a notebook computer.

As shown in FIG. 1A, the virtual space server 12 (i.e., an example of an information processing apparatus according to an embodiment) may obtain sound signals from multiple sound collection apparatuses 11 disposed at different positions in a real space. The virtual space server 12 may obtain sound source information of a sound source in a real space through appropriate processing based on the sound signals, and may obtain a sound field in a virtual space based on the sound source information and virtual space information of the virtual space server by using a sound field synthesis model pre-obtained through machine learning.

In an implementation, the virtual space server 12 may further obtain user information from the terminal device 13 of a user (where the user information may include: a position of the user in the virtual space, such as a position in the virtual space expected or specified by the user; information about a physiological attribute of the user; and the like), and generate and output a sound signal suitable for the user based on the sound field in a virtual space and the user information, so that the terminal device 13 may provide, based on the sound signal, the user with a sound output having a high degree of reality and high real-time performance.

FIG. 1B is a modified example of an information processing system as shown in FIG. 1A. FIG. 1B is different from FIG. 1A in that: the terminal device 13 has a strong processing capability and can be implemented as an information processing apparatus according to an embodiment of the present disclosure, and therefore implements the function of generating the virtual space sound field and the function of generating and outputting the sound signal suitable for the user, similar to the virtual space server 12 in FIG. 1A. The terminal device 13 in FIG. 1B obtains, from the virtual space server 12, the sound signals received from the sound collection apparatus 11 and the virtual space information, and combines the same with the user information of the terminal device, so as to perform the above-mentioned functions.

Here, although a head-mounted display, a mobile phone, and a notebook computer are shown as examples of the terminal device 13 in FIG. 1A and FIG. 1B, the present disclosure is not limited thereto. The terminal device may be a tablet computer, a general-purpose personal computer, and the like, which is not described in detail here.

Next, the information processing system of FIG. 1A is taken as an example, and the apparatus and method according to embodiments of the present disclosure are further described in conjunction with the drawings. It is to be noted that the apparatus and method in the following embodiments can be appropriately applied to the situation of FIG. 1B. That is, although description is made in the following embodiments in conjunction with an example case in which the information processing apparatus/method is implemented at the virtual space server 12 of FIG. 1A, the information processing apparatus/method in the following embodiments may also be appropriately implemented at the terminal device 13 in FIG. 1B, which is not described in detail here.

2. Exemplary Configuration of an Information Processing Apparatus

2.1 Example of a Basic Configuration

Figure 2:
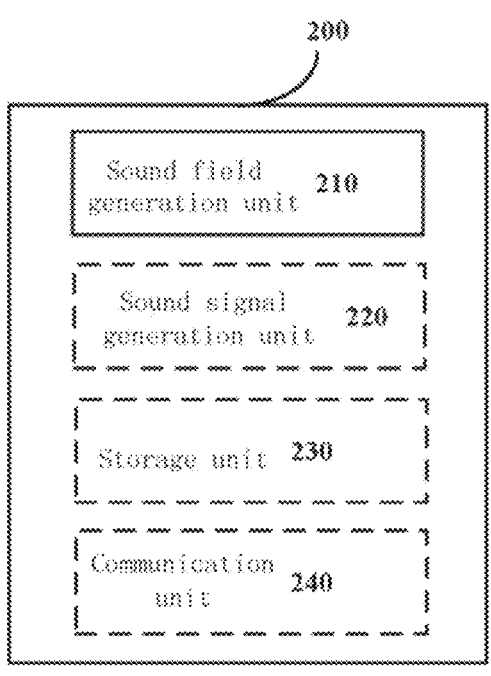
FIG. 2 is a block diagram illustrating an exemplary configuration of an information processing apparatus according to an embodiment of the present disclosure.

FIG. 2 is a block diagram illustrating an exemplary configuration of an information processing apparatus according to an embodiment of the present disclosure.

As shown in FIG. 2, the information processing apparatus 200 may include a sound field generation unit 210 and optionally a sound signal generation unit 220, a communication unit 230 and a storage unit 240. The communication unit 230 may be configured for communication between the information processing apparatus and other devices, and the storage unit 240 may be configured for storage of various programs, data, information, and the like.

Here, units of the information processing apparatus 200 may be included in processing circuitry. It should be noted that the information processing apparatus 200 may include a single processing circuit or multiple processing circuits. Further, the processing circuitry may include various discrete functional units for performing various different functions and/or operations. It should be noted that these functional units may be physical entities or logical entities, and units with different names may be implemented by a same physical entity.

As an example, the information processing apparatus 200 may obtain, through the communication unit 230, sound signals from multiple sound collection devices disposed at different positions in a real space, and the sound field generation unit 210 may perform appropriate processing (such as, but not limited to, a blind sound source detection) based on the sound signals to obtain sound source information of a sound source in a real space. The sound source information indicates a position of the sound source and the sound signals.

Furthermore, for example, the information processing apparatus 200 may have virtual space information stored in the storage unit 240. The virtual space information indicates, for example, an object present in a virtual space, such as a position and an attribute (such as volume, height, and surface material/texture) of the object.

According to an embodiment of the present disclosure, the sound field generation unit 210 of the information processing apparatus 200 may be configured to: obtain a sound field in a virtual space, by using a sound field synthesis model, based on sound source information about a sound source in a real space and virtual space information indicating an object present in a virtual space. Here, the sound field synthesis model is pre-obtained through machine learning by using a sound field in a virtual space obtained from high-precision calculation as learning data.

The information processing apparatus 200 may obtain the sound field synthesis model in advance and store the sound field synthesis model in the storage unit 240. Preferably, the sound field synthesis model may be based on a convolutional neural network (CNN). As an example, the sound field generation unit 210 of the information processing apparatus 200 may generate a sound field synthesis model such as a CNN model through machine learning via a training module (described later) included therein by using a sound field in a training virtual space as learning data. The sound field in a training virtual space is obtained from high-precision calculation based on information of a training sound source in a real space, a spatial structure of the training virtual space.

Optionally, the information processing apparatus 200 may further include a sound signal generation unit 220, which may be configured to: generate a sound signal suitable for a user based on user information such as a position of the user and the sound field in the virtual space. For example, the sound signal generation unit 220 may determine a sound signal at a corresponding position of the sound field in a virtual space as the sound signal suitable for the user based on, for example, information about of a position of the user in the virtual space specified by the user.

The example of the basic configuration of the information processing apparatus of the embodiment of the present disclosure is described above with reference to FIG. 2. With the information processing apparatus 200 according to the embodiment, the virtual space sound field having a high degree of reality and high real-time performance can be generated, and optionally the sound signal of the sound field suitable for the user can be generated. In this way, user experience of the virtual space can be improved.

Next, an exemplary configuration of the sound field generation unit 210 and the signal generation unit 220 as in FIG. 2 and an example process thereof are described.

2.2 Exemplary Configuration of a Sound Field Generation Unit

Figure 3:
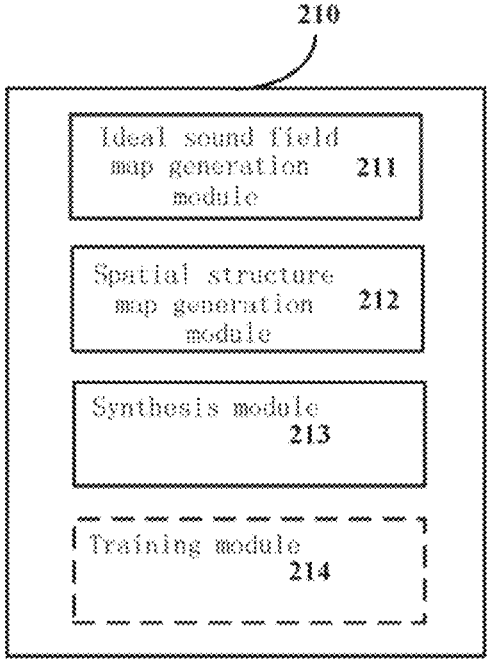
FIG. 3 is a block diagram showing an exemplary configuration of a sound field synthesis unit in FIG. 2.

FIG. 3 is a block diagram showing an exemplary configuration of a sound field generation unit 210 in FIG. 2.

As shown in FIG. 3, the sound field generation unit 210 may include an ideal sound field map generation module 211, a spatial structure map generation module 212, a synthesis module 213 and optionally a training module 214.
(Ideal Sound Field Map Generation Module)

The ideal sound field map generation module 211 may be configured to generate an ideal sound field map representing an ideal sound field in a virtual space without an object (that is, in a case where there is no obstacle that hinder propagation of sound), based on the sound source information about a sound source in a real space.

As an example, the ideal sound field map generation module 211 may obtain sound signals which are obtained by the information processing apparatus 200 through a communication unit from multiple sound collection apparatuses, such as microphones, disposed at different positions in a real space, and may perform blind sound source detection or other processing based on the sound signals to obtain the sound source information of a sound source in a real space.

As an example, the ideal sound field map generation module 211 may first obtain respective sound signals of individual sound sources from sound signals of multiple microphones at known positions by using a filter-and-sum network (FasNet) or a multi-channel wave-U-Net, to obtain, for example, sound signals $w_1(t), \ldots, w_K(t)$(that is, $w_K(t)$, $k=1, \ldots, K$) of K sound sources changing with time. Then, the ideal sound field map generation module 211 may determine positions of the sound sources based on attenuation of the sound sources according to relative magnitude relationship of the sound signals of the sound sources received by the microphones. In this way, the ideal sound field map generation module 211 can determine sound signals and positions of the sound sources, respectively. In addition, the ideal sound field model may map the positions of the sound sources in a real space to corresponding positions in a virtual space based on a predefined mapping rule from the real space to the virtual space, so as to obtain the positions of the sound sources in the virtual space.

Based on the obtained sound signals $w_k(t)$ of the K sound sources and the positions of the sound sources, the ideal sound field map generation module 211 may perform linear superposition of the sound signals of the sound sources after performing point source attenuation, and determine an ideal sound signal $S_p(t)$ at position P which is at a distance $r_{kp}$ from a sound source $w_k(t)$ in the virtual space through the following equation (1):

$$S_P(t) = \sum_{k=1}^{K} w_k(t)\Delta L_k = \sum_{k=1}^{K} w_k(t)\log(1/\pi r_{kP}^2) \qquad (1)$$

In the equation, $\Delta L_k = \log(1/\pi r_{kP}^2)$ represents attenuation, at position P, of sound source $w_k(t)$.

Figure 7:
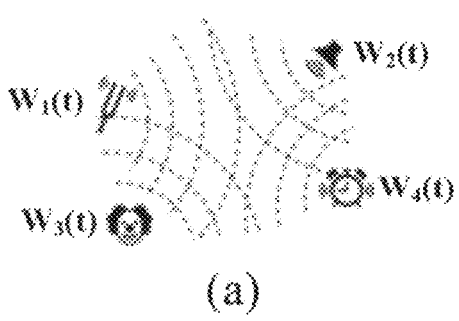
FIG. 7 is a schematic diagram illustrating an exemplary process of a unit and/or module of an information processing apparatus as shown in FIG. 2.
Figure 7:
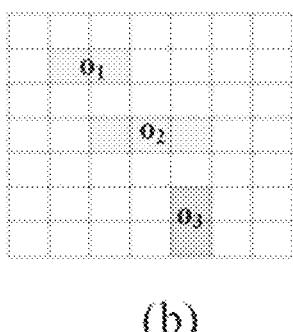
Figure 7:
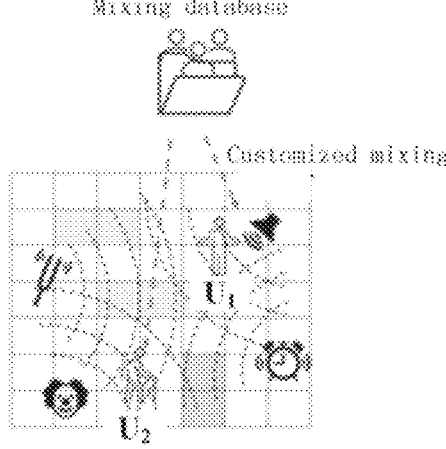

In this way, the ideal sound field map generation module 211 may obtain ideal sound signals at respective positions in the virtual space, and thereby obtain the ideal sound field $\{S_p(t), P \in V\}$ in the virtual space, where V represents a set of all positions in the virtual space. In FIG. 7, (a) shows a schematic diagram of an example of an ideal sound field, which represents four sound sources $w_1(t)$ to $w_4(t)$ at different positions. In order to simplify the description, a time expression (t) in symbols of sound signals may be omitted hereinafter in some cases.

The ideal sound field map generation module 211 may generate an ideal sound field map IMap(P) representing an ideal sound field in a virtual space without an object, based on the ideal sound field $\{S_P, P \in V\}$ generated through above manner. In the Imap(P), each position P has a value corresponding to a sound signal $S_P$ of the ideal sound field at this position. For example, but is not limited to, the value is a pixel value such as a grayscale value corresponding to the sound signal $S_P$. Optionally, the mapping relationship between values of ideal sound fields (i.e., values of the sound signals) and grayscale values as an example of pixel values may be pre-determined, for example, through normalization, which is not described in detail here.

In this example, to simplify the description, a virtual space including two-dimensional positions is taken as an example, that is, each position P in the virtual space is represented by a two-dimensional coordinate (x, y). In such an example, the ideal sound field map generation module 211 may generate an ideal sound field map IMap (x, y), for example, in a form of a grayscale map, based on the ideal sound field $\{S_P, P \in V\}$, where a grayscale value of a position P=(x, y) is determined based on a value of the sound signal $S_P$ of the ideal sound field at this position. Preferably, the ideal sound field map generated by the ideal sound field map generation module 211 is a grid map gridded with a predetermined resolution. The resolution may be consistent with a resolution of a spatial structure map described later, and may be, for example, 0.1 meter/grid.
(Spatial Structure Map Generation Module)

The spatial structure map generation module 212 may be configured to: generate a spatial structure map representing a spatial structure of the virtual space based on the virtual space information indicating a position and an attribute of an object in the virtual space. For example, the spatial structure map may be generated by marking the position and the attribute of the object in a virtual spatial map.

The virtual space information may indicate a position of an object in the virtual space that may be considered as an obstacle to sound propagation and an attribute of the object. As an example, the above-mentioned attribute may be an attribute of the object related to hindering the sound propagation (obstacle attributes), such as a volume, height, surface material/texture (smoothness/density) of the object.

In order to facilitate marking in the virtual space map, as an example, the spatial structure map generation module 212 may calculate an obstacle attribute $O_n$ of each object according to a predetermined rule based on attributes of N objects indicated by the virtual space information, where $n=1, \ldots$ , N. Thereby, the attribute can comprehensively represent a degree of obstruction of the object to sound propagation. For example, the predetermined rule may include that: the spatial structure map generation module 212 sets a greater obstacle attribute value for an object having a greater volume, a greater height, a smoother and/or denser surface.

The spatial structure map generation module 212 may mark, for example, the obstacle attribute value calculated through the above manner as a spatial attribute value at a position of an object in the virtual space map, and mark 0 as the spatial attribute value at a position where no object exists, so as to generate the spatial structure map.

That is, the spatial structure map generation module 212 may determine a spatial attribute value $A_P$ of a position P in the virtual space through the following equation (2):

$$A_P = \begin{cases} O_n, & \text{there is object } n \text{ at position } P \\ 0, & \text{there is no object at position } P \end{cases} \qquad (2)$$

The spatial structure map generation module 212 may generate a spatial structure map AMap(P) representing a spatial structure of the virtual space based on the obtained spatial attribute $\{A_P, P \in V\}$ of the positions, where each position P has a value corresponding to a spatial attribute value $A_P$ of the spatial structure map at the position, for example, a pixel value such as grayscale corresponding to $A_P$. Optionally, a mapping relationship between the spatial attribute values of the positions and grayscale values as an example of the pixel value may be pre-determined, for example, through normalization, which is not described in detail here.

In this example, to simplify the description, a two-dimensional virtual space is taken as an example, and each position P in the virtual space is represented by a two-dimensional coordinate (x, y). Therefore, the spatial structure map generation module 212 may generate the spatial structure map in a form of a two-dimensional grayscale image. Preferably, the spatial structure map generated by the spatial structure map generation module 212 is a grid map gridded with a predetermined resolution, and the resolution is consistent with the resolution of the ideal sound field map generated by the ideal sound field map generation module 211 (for example, 0.1 meter/grid), in order to facilitate subsequent processing by the synthesis module 223. In FIG. 7, (b) schematically shows an example of the generated spatial structure map.

(Synthesis Module)

The synthesis module 213 may be configured to: input the ideal sound field map and the spatial structure map with a same resolution into the sound field synthesis model to obtain the sound field in a virtual space outputted from the sound field synthesis model. As an example, the synthesis module 213 may superpose the ideal sound field map and the spatial structure map one on the other, which have a same resolution and are easily to be aligned, and then input the same into the sound field synthesis model.

In a preferred example, the sound field synthesis model utilized by the synthesis module 213 is a CNN model pre-obtained by the training module 214 through machine learning and stored in the storage unit 240. Preferably, the CNN model may be based on a deep neural network (DNN), a convolution operator of the CNN model may be 3D depth separable convolution, and a network structure thereof may be a V-Net. Such configuration is beneficial to improving a processing speed, efficiency and accuracy of the model.

As an example, the sound field in a virtual space outputted by the sound field synthesis model may be a set of synthesized sound signals $B_P(t)$ at each position P, that is $\{B_P(t), P \in V\}$. Here, $B_P(t)$ may be an actual value of the sound signal or other values that can represent the actual value.

(Training Module)

Optionally, the training module 214 may be configured to: obtain a sound field in a training virtual space through high-precision calculation based on information about a training sound source in a real space and a spatial structure of the training virtual space, and obtain the sound field synthesis model in advance through machine learning by using the sound field as learning data.

For example, the training module 214 may first set multiple sets of training object data. Each set of training object data includes different positions of sound sources, sound signals of the sound sources (i.e., different waveforms), and a virtual space map and objects therein. The training module 214 may calculate an ideal sound field map and a spatial structure map of each set of training object data through the ideal sound field map generation module 211 and the spatial structure map generation module 212, and input, through the synthesis module 213, the ideal sound field map and the spatial structure map to a CNN-based synthesis model for training.

In addition, the training module 214 performs high-precision simulation of the virtual space sound field for each set of training object data by using high-precision sound field simulation software (such as Matlab, Raynoise, Actran and other sound field simulation software). A simulation result is the learning data after the high-precision calculation and is a training target for the synthesis model.

The training module 214 may use a mean square error as a loss function for characterizing a difference between an output result of the synthesis model for each set of training object data and the respective training target, and train the CNN-based synthesis model by using a standard CNN training technique to determine parameters of the synthesis model, which is not described in detail here.

2.3 Exemplary Configuration of Sound Signal Generation Unit

Figure 4:
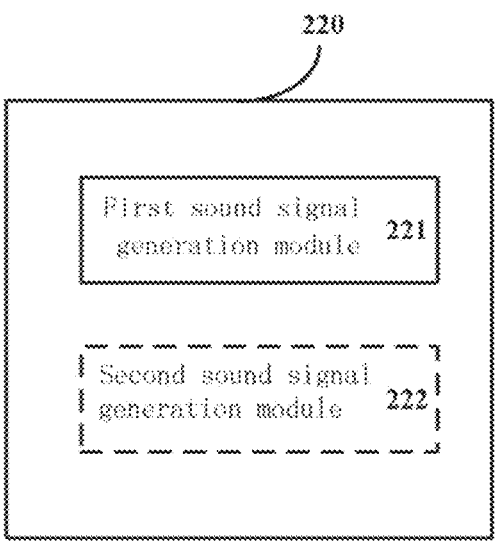
FIG. 4 is a block diagram showing an exemplary configuration of a sound signal generation unit in FIG. 2.

FIG. 4 is a block diagram showing an exemplary configuration of a sound signal generation unit in FIG. 2.

As shown in FIG. 4, the sound signal generation unit 220 may include a first sound signal generation module 221 and optionally a second sound signal generation module 222.

(First Sound Signal Generation Module)

The first sound signal generation module 221 may be configured to generate a first sound signal based on the sound field in a virtual space and a position of a user.

As an example, the first sound signal generation module 221 may determine a first sound signal $B_U(t)=B_{P=U}(t)$ for a user, based on a user position U (i.e., a position in the virtual space expected or specified by the user) obtained by the information processing apparatus 200 from a terminal device of the user via the communication unit and the sound field $\{B_P(t), P \in V\}$ in the virtual space generated by the sound field generation unit. In this way, a real sound experience can be provided to the user at different positions in the virtual space.

Here, for example, in a case of a three-dimensional virtual space, the user position U may be a position where the head of the is located (that is, heights of different users are taken into account). In this way, a more refined and customized sound experience can be provided.

(Second Sound Signal Generation Module)

The second sound signal generation module 222 may be configured to mix the first sound signal with a mixing scheme (mixing mode) suitable for the user based on a physiological attribute of the user to generate a second sound signal. Next, an exemplary configuration of the second sound signal generation module is described with reference to FIG. 5.

Figure 5:
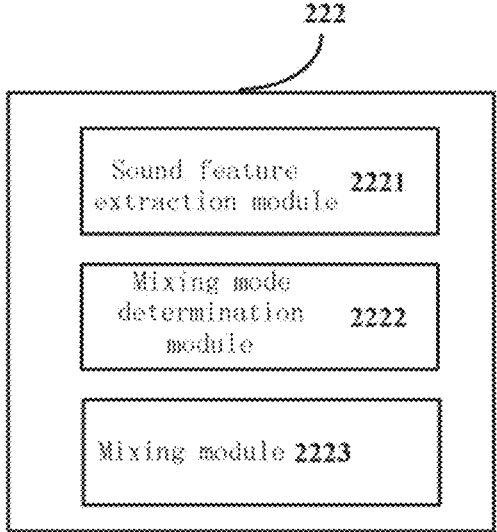
FIG. 5 is a block diagram showing an exemplary configuration of a second sound signal generation module in FIG. 4.

FIG. 5 is a block diagram showing an exemplary configuration of a second sound signal generation module in FIG. 4. As shown in FIG. 5, the second sound signal generation module 222 may include a sound feature extraction module 2221, a mixing mode determination module 2222, a mixing module 2223, and optionally a training module (not shown).

The sound feature extraction module 2221 may extract an auditory feature of the user based on a physiological attribute of the user by using an auditory feature extraction model.

Here, the sound feature extraction module 2221 may obtain the physiological attribute of the user, from physiological attribute information such as an age, gender, and/or an image containing an ear of the user included in the user information obtained from the terminal device by the information processing apparatus 200 via the communication unit 230. The physiological attribute may include one or more of the age, gender, and ear morphological feature of the user.

As an example, the sound feature extraction module 2221 may detect an ear part from the image containing an ear by using an image processing algorithm, perform registration (zoom to a standard size and rotate to a standard angle) on the image and then input it into a pre-obtained ear morphological feature extraction model for extracting the ear morphological feature. As an example, the ear morphological feature extraction model may be a CNN model that is trained from a large-scale public data set and is able to extract the Haar feature in a form of vector.

The sound feature extraction module 2221 may input the physiological attribute of the user (including the age, gender and/or ear morphological feature of the user, for example) obtained in the above manner into a pre-obtained auditory feature extraction model for extracting an auditory feature of the user through the model. As an example, the auditory feature may be in a form of vector.

Here, the auditory feature extraction model may be pre-stored in the storage unit 240. The auditory feature extraction model may be obtained through metric learning, for example, by a not-shown training module from historical data of physiological attributes and mixing modes which are pre-obtained and correlated with each other. The model may extract the auditory feature from the inputted physiological attribute of the user. A similarity between extracted auditory features of users can reflect a similarity between the mixing schemes for the users.

The metric learning perform by the training model aims to train the auditory feature extraction model so that a similarity between the auditory feature extracted from the inputted physiological attributes of the users can reflect a similarity between the mixing schemes for the users. The training module may train the constructed model, such as a CNN model, through various existing methods for metric learning, by using historical data of correlated physiological attributes and mixing modes to obtain the required model.

For example, a case of two mixing schemes Ms1 and Ms2 is taken as an example in order to simplify the description. It is assumed that the two mixing schemes correspond to physiological attributes c1 and c2, respectively, and a similarity between Ms1 and Ms2 is represented as Sim(Ms1, Ms2). In this case, in order to train a deep neural network DNN as the auditory feature extraction model, the training module may construct a loss function loss as follows:

$$\text{loss} = [DNN(c1) - DNN(c2)]^2 - \text{Sim}(Ms1, Ms2)^2 \qquad (3)$$

The training module may minimize the loss function loss by training DNN to obtain optimal parameters of the model. For a case of more mixing schemes, the training module may similarly implement the training of the auditory feature extraction model according to a similar principle, which is not described in detail here.

Here, the similarity between two mixing schemes may be calculated by using a distance between coefficients of filters corresponding to the two mixing schemes (for example, an average of distances of the coefficients). Common mixing modes (or mixing schemes) include, for example, superimposing different instruments and vocal tracks at similar volumes, removing a sound having a low frequency (such as <50 Hz), enhancing sounds having different frequencies at different levels, and the like. A principle of a mixing scheme is to filter an inputted sound signal by using band-pass filters. Therefore, a mixing scheme may be represented by a set of filters, and a difference between coefficients of two sets of filters may represent a similarity between mixing schemes.

The mixing mode determination module 2222 may select at least one mixing mode from a database (also referred to as a mixing database, which is pre-stored in the storage unit 240 of the information processing apparatus 200, for example) based on the auditory features extracted by the sound feature extraction module 2221 using the auditory feature extraction model stored in the storage unit 240, and determine a mixing mode for the user based on the selected mixing mode.

Here, the mixing database may be pre-obtained by: extracting the auditory feature of each piece of historical data from the historical data of physiological attributes and mixing modes associated with each other by using the auditory feature extraction model stored in the storage unit 240, and then storing the auditory feature and the mixing mode of each piece of historical data in association with each other as mixing data.

The mixing mode determination module 2222 may using the auditory feature extracted for a current user to select, based on a similarity between the extracted auditory feature and the auditory feature of each piece of mixing data in the mixing database, a predetermined number of mixing schemes (similar mixing schemes) of mixing data having auditory features of the highest similarity (similar auditory features); and then perform linear interpolation on the similar mixing schemes based on a similarity between the auditory feature extracted for the current user (current auditory feature) and each of the similar auditory features, to obtain a mixing mode for the user. The similarity between two auditory features may be calculated, for example but not limited to, based on a distance (such as a cosine distance or Euclidean distance) between vectors of the two auditory features.

In an example, the mixing module 2223 may adopt mixing modes of three similar auditory features V1 to V3 in the mixing database that are closest to the current auditory feature V, and perform linear interpolation based on the concerned similarity to obtain a mixing scheme for the current auditory feature V.

Figure 6:
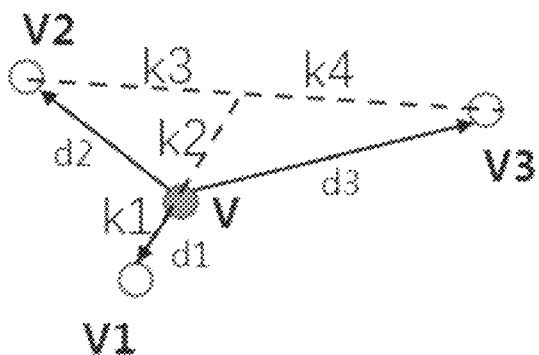
FIG. 6 is a schematic diagram illustrating an exemplary process of determining a mixing mode.

FIG. 6 shows an example of the linear interpolation, in which the solid circle and open circles represents the current auditory feature V and the similar auditory features V1 to V3 in the vector space, respectively. Weight coefficients $k_1$ to $k_4$ for the linear interpolation may be calculated based on distances $d_1$, $d_2$, $d_3$ between the current auditory feature V and the similar auditory features V1, V2, V3. For example, the weight coefficients $k_1$ to $k_4$ may be equal to lengths of corresponding line segments shown in FIG. 6, that is, $k_1=d_1$, and $k_2$, $k_3$, $k_4$ are determined based on intersection points of an extension line of a segment connecting V and V1 and a segment connecting V2 and V3. As shown in the figure, $k_2$ is a distance from the current auditory feature V to the intersection point, $k_3$ and $k_4$ are distances from the similar auditory features V2 and V3 to the intersection point, respectively. The above distances may be obtained through simple geometric calculation based on positions of the auditory features in the vector space and the distances $d_1$ to $d_3$, which is not described in detail here. Here, it is assumed that the mixing schemes of the auditory features V1, V2, and V3 are expressed as coefficients $F_{11}, \ldots, F_{1M}, F_{21}, \ldots, F_{2M}$, and $F_{31}, \ldots, F_{3M}$ of M filters, respectively. Hence, the interpolation may be performed by using the weight coefficients $k_1$ to $k_4$ according to the following equation (4), so as to determine a coefficient of the m-th filter $F_m$ of the mixing scheme for the current user as:

$$F_m = \frac{k_2}{k_1 + k_2} F_{1m} + \frac{k_1}{k_1 + k_2} \left[ \frac{k_4}{k_3 + k_4} F_{2m} + \frac{k_3}{k_3 + k_4} F_{3m} \right] \quad (4)$$

The mixing module 2223 may perform mixing on the (first) sound signal of the user in the calculated mode, so as to generate the (second) sound signal (output sound signal) to be outputted to the user.

In this way, the generated sound signal additionally takes into account the physiological attribute such as gender, age, ear shape of the user. Therefore, a sound experience with further enhanced high degree of reality can be provided to the user.

In FIG. 7, (c) schematically illustrates an effect of a sound signal suitable for the user in the virtual space generated by the sound signal generation unit 220 through processing of respective modules. That is, the sound signal generation unit 220 generates the first sound signals for users at different positions U1 and U2 in the virtual space sound field, which represents influences of sound sources and obstacles and is generated based on the ideal sound field map and the spatial structure map, and it performs customized mixing on the first signal in a manner suitable for each user to obtain a second sound signal (output sound signal) suitable for each of the users.

2.4 Exemplary Application Scenario

Next, an exemplary application scenario of the information processing system as shown in FIG. 1A is described, in which the virtual space server 12 has a configuration and function as the information processing apparatus 200 described above in conjunction with FIG. 2.

(Sound Presentation Synchronized with Offline Exhibition)

An exemplary application scenario of the information processing system in FIG. 1A is to provide an immersive sound experience to users in a virtual space such as the Metaverse simultaneously with an offline exhibition.

In this exemplary scenario, in order to provide a sound experience consistent with offline, the virtual space server 12 is required to collect and play sound from visitors (such as discussions, opinions), in addition to collecting and playing sound from exhibitors (such as product introductions). The virtual space server 12 may perform complex collection of offline sounds by using multiple sound collection apparatuses 11 as shown in FIG. 1A, and may obtain the sound source information of the exhibitors and the visitors based on the sounds, generate the sound field in a virtual space based on the sound source information and the virtual space information, and then provide a realistic and immersive sound experience based on positions of different users in the virtual space such as the metaverse (where the positions may have a corresponding relationship with offline positions) and auditory features of the users.

(Sound Presentation Synchronized with Offline Music Festival)

An exemplary application scenario of the information processing system in FIG. 1A is to provide an immersive sound experience to users in a virtual space such as the Metaverse simultaneously with an offline music festival.

Similar to the previous exemplary scenario, in order to provide a sound experience consistent with offline, the virtual space server 12 is required to collect and play sound from audience, in addition to collecting and playing sound on a stage. The virtual space server 12 may collect sounds by using multiple sound collection apparatuses 11 as shown in FIG. 1A, and may obtain the sound source information of on-stage and off-stage based on the sounds, generate the sound field in a virtual space based on the sound source information and the virtual space information, and then provide a realistic and immersive sound experience based on positions of different users in the virtual space such as the metaverse (where the positions may have a corresponding relationship with offline positions) and auditory features of the users. In this way, in a case that a user of the Metaverse is between several stages, the user can not only hear music on the stages, but also hear cheers of the audience and other sounds, thereby experiencing a better atmosphere of the music festival.

3. Method Embodiment

Corresponding to the apparatus embodiments, the present disclosure provides the following method embodiments.

Figure 8:
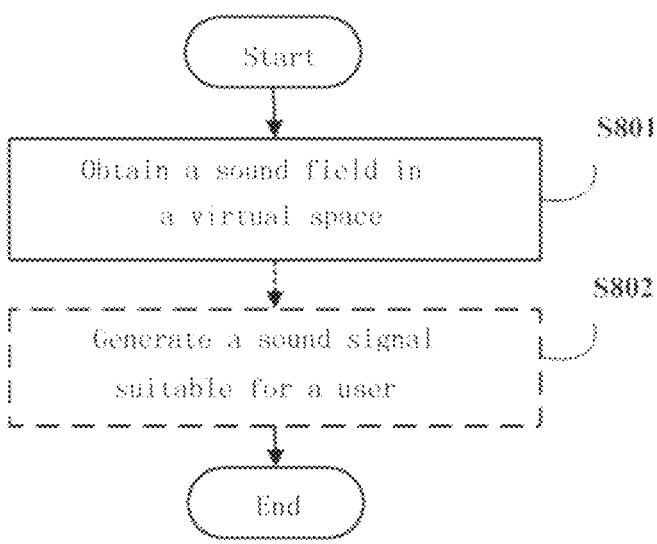
FIG. 8 is a flowchart illustrating an exemplary process of an information processing method according to an embodiment of the present disclosure.

FIG. 8 is a flowchart illustrating an exemplary process of an information processing method according to an embodiment of the present disclosure.

Reference is made to FIG. 8. In step S801, a sound field in a virtual space is obtained by using a sound field synthesis model, based on sound source information about a sound source in a real space and virtual space information indicating an object present in a virtual space. Here, the sound field synthesis model is pre-obtained through machine learning by using a sound field in a virtual space obtained from high-precision calculation as learning data.

Optionally, high-precision calculation is performed based on information about a training sound source in the real space and a spatial structure of a training virtual space, so as to obtain a sound field in a training virtual space as the learning data. Optionally, the sound field synthesis model is a model based on a convolutional neural network.

Optionally, as an example, an ideal sound field map representing an ideal sound field in a virtual space without an object may be generated based on the sound source information about a sound source in a real space. Optionally, a spatial structure map representing a spatial structure of the virtual space may be generated based on the virtual space information indicating a position and an attribute of an object in the virtual space. Optionally, the ideal sound field map and the spatial structure map with a same resolution may be inputted into the sound field synthesis model to obtain the sound field in a virtual space outputted from the sound field synthesis model.

Next, in an optional step S802, a sound signal suitable for a user may be generated based on a position of the user and the sound field in a virtual space.

Although not shown in FIG. 8, in the exemplary process of FIG. 8, the method may further include (during or before step S801) a step of determining a sound source in the real space through blind sound source detection based on sound signals obtained from multiple sound collection apparatuses at different positions in the real space, to obtain the sound source information.

In addition, although not shown in FIG. 8, in the example process of FIG. 8, the method may further include (during or after step S802) steps of: extracting an auditory feature of the user based on a physiological attribute of the user by using an auditory feature extraction model; selecting, based on the extracted auditory feature, at least one mixing modes from a database which stores auditory features and mixing modes in association with each other; determining a mixing mode for the user based on the selected mixing mode; and performing mixing on the sound signal in the determined mode to generate a sound signal to be outputted to the user.

As an example, the physiological attribute of the user may include one or more of age, gender, and an ear morphological feature of the user. Here, the auditory feature extraction model may be obtained through metric learning by using pre-obtained historical data of physiological attributes and mixing modes in association with each other.

According to an embodiment of the present disclosure, a subject that performs the method may be the information processing apparatus 200 according to the embodiment of the present disclosure. Therefore, the previous embodiments of the information processing apparatus are applicable here and are not repeated here.

4. Application Example

The technology of the present disclosure is applicable to various products.

For example, the information processing apparatus according to the embodiments of the present disclosure may be implemented as any type of control entity, such as a tower server, a rack server, a blade server and other servers. The information processing apparatus 200 (and the information processing apparatus in the fourth configuration) may be a control module installed on a server (such as an integrated circuit module including a single wafer, and a card or blade inserted into a slot of a blade server).

In addition, the information processing apparatus in the configuration according to the embodiments of the present disclosure may be implemented as a user device. For example, the apparatus may be implemented as a mobile terminal (such as a smartphone, a tablet personal computer (PC), a notebook PC, a portable game terminal, a portable/dongle-type mobile router, a digital camera, and a head-mounted display), or an in-vehicle terminal (such as a car navigation device). The user device may also be implemented as a terminal that performs machine-to-machine (M2M) communication (which is also referred to as a machine type communication (MTC) terminal).

Application Examples of Control Entity

Figure 9:
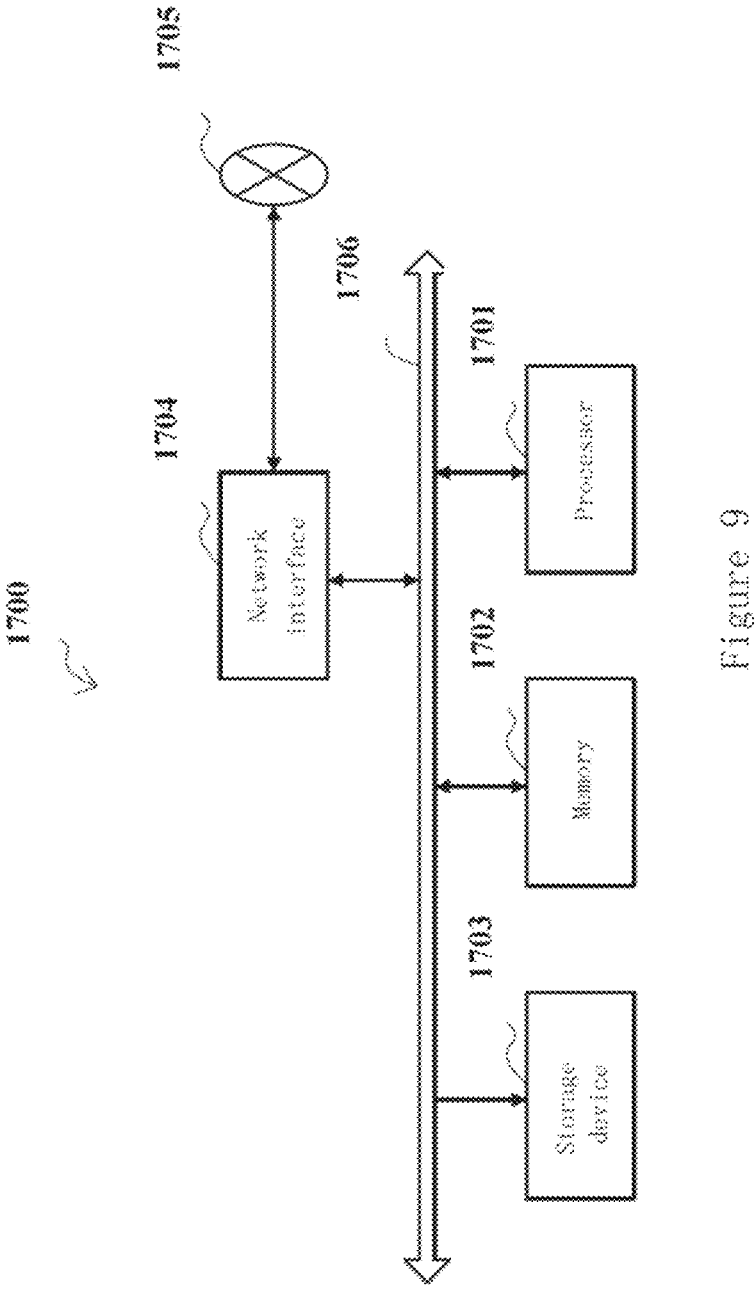
FIG. 9 is a block diagram showing an example of a schematic configuration of a server to which the technology of the present disclosure may be applied.

FIG. 9 is a block diagram showing an example of a schematic configuration of a server 1700 to which the technology of the present disclosure may be applied. The server 1700 includes a processor 1701, a memory 1702, a storage device 1703, a network interface 1704, and a bus 1706.

The processor 1701 may be, for example, a central processing unit (CPU) or a digital signal processor (DSP), and controls functions of the server 1700. The memory 1702 includes a random-access memory (RAM) and a read-only memory (ROM), and stores data and a program executed by the processor 2201. The storage device 1703 may include a storage medium, such as a semiconductor memory and a hard disk.

The network interface 1704 is a wired communication interface for connecting the server 1700 to a wired communication network 1705. The wired communication network 1705 may be a core network such as an Evolved Packet Core (EPC), or a packet data network (PDN) such as the Internet.

The bus 1706 connects the processor 1701, the memory 1702, the storage device 1703, and the network interface 1704 to each other. The bus 1706 may include two or more buses having different speeds (such as a high-speed bus and a low-speed bus).

In the server 1700 shown in FIG. 9, at least part of functions of the sound generation unit and the sound signal generation unit of the information processing apparatus 200 described with reference to FIG. 2 may be implemented by the processor 1701. For example, the processor 1701 may perform at least part of functions of the above-mentioned units by executing instructions stored in the memory 1702 or the storage device 1703. Furthermore, the communication unit in the information processing apparatus 200 may be implemented via the network interface 1704 or the like. Furthermore, the storage unit in the information processing apparatus 200 may be implemented via the memory 1702, the storage device 1703, or the like.

Application Examples of User Equipment

First Application Example

Figure 10:
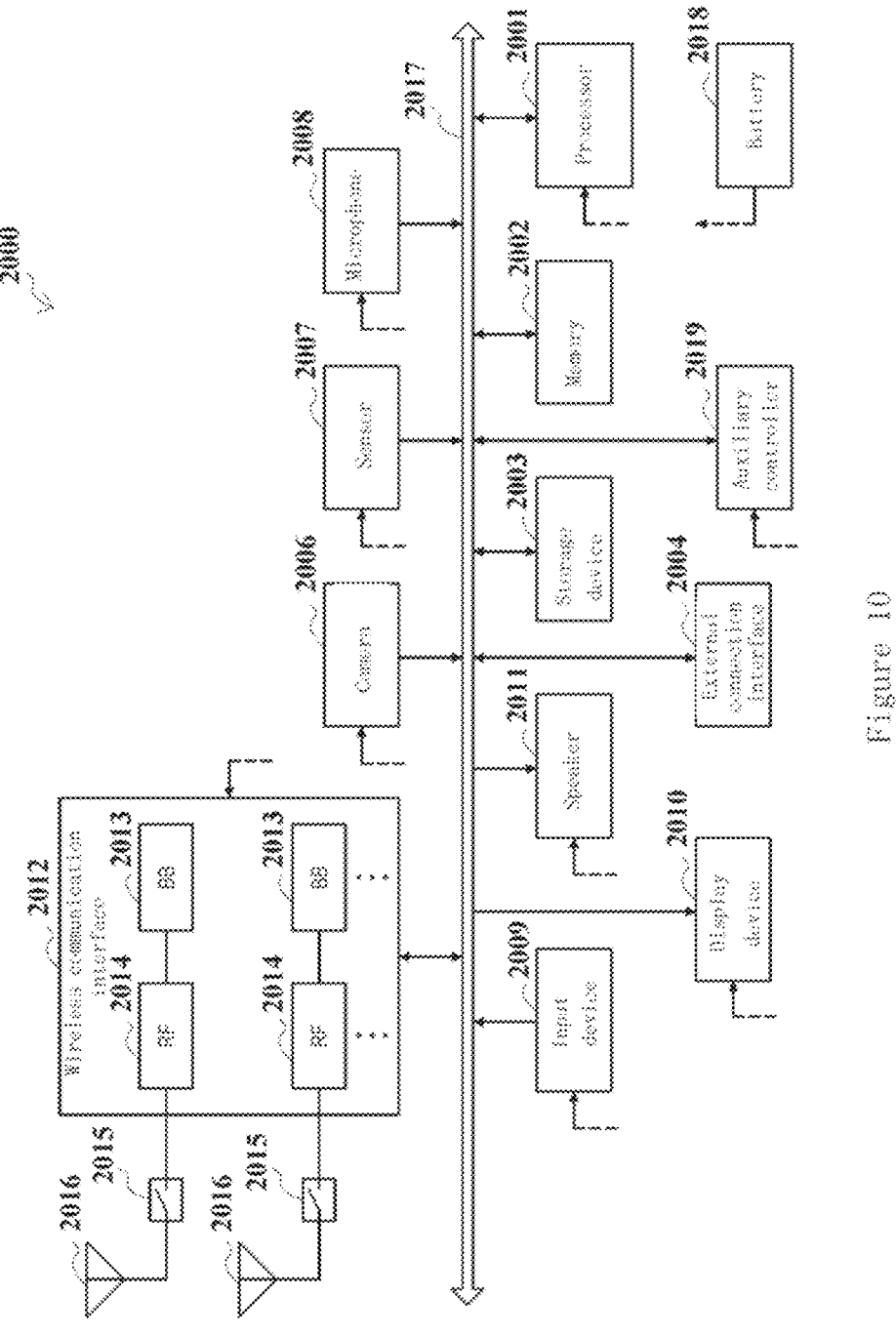
FIG. 10 is a block diagram showing an example of a schematic configuration of a smartphone to which the technology of the present disclosure may be applied.

FIG. 10 is a block diagram showing an example of a schematic configuration of a smartphone 2000 to which the technology of the present disclosure may be applied. The smartphone 2000 includes a processor 2001, a memory 2002, a storage device 2003, an external connection interface 2004, a camera device 2006, a sensor 2007, a microphone 2008, an input device 2009, a display device 2010, a speaker 2011, a wireless communication interface 2012, one or more antenna switches 2015, one or more antennas 2016, a bus 2017, a battery 2018, and an auxiliary controller 2019.

The processor 2001 may be, for example, a CPU or a system on a chip (SoC), and controls the functions of the application layer and other layers of the smartphone 2000. The memory 2002 includes a RAM and a ROM, and stores data and programs executed by the processor 2001. The storage device 2003 may include a storage medium such as a semiconductor memory and a hard disk. The external connection interface 2004 is an interface for connecting an external device, such as a memory card or a universal serial bus (USB) device, to the smartphone 2000.

The camera device 2006 includes an image sensor (such as a charge coupled device (CCD) and a complementary metal oxide semiconductor (CMOS)), and generates a captured image. The sensor 2007 may include a group of sensors, such as a measurement sensor, a gyroscope sensor, a geomagnetic sensor, and an acceleration sensor. The microphone 2008 converts sound inputted to the smartphone 2000 into an audio signal. The input device 2009 includes, for example, a touch sensor, a keypad, a keyboard, a button, or a switch configured to detect a touch on a screen of the display device 2010, and receives an operation or information inputted from a user. The display device 2010 includes a screen, such as a liquid crystal display (LCD) or an organic light emitting diode (OLED) display, and displays an output image of the smartphone 2000. The speaker 2011 converts the audio signal outputted from the smartphone 2000 into sound.

The wireless communication interface 2012 supports any cellular communication scheme (such as LTE and LTE-Advanced), and performs wireless communication. The wireless communication interface 2012 may generally include, for example, a BB processor 2013 and an RF circuit 2014. The BB processor 2013 may perform, for example, encoding/decoding, modulation/demodulation, and multiplexing/demultiplexing, and perform various types of signal processing for wireless communication. Further, the RF circuit 2014 may include, for example, a mixer, a filter, and an amplifier, and transmit and receive wireless signals via the antenna 2016. The wireless communication interface 2012 may be a chip module on which a BB processor 2013 and an RF circuit 2014 are integrated. As shown in FIG. 10, the wireless communication interface 2012 may include multiple BB processors 2013 and multiple RF circuits 2014. Although FIG. 10 shows an example in which the wireless communication interface 2012 includes multiple BB processors 2013 and multiple RF circuits 2014, the wireless communication interface 2012 may include a single BB processor 2013 or a single RF circuit 2014.

In addition to the cellular communication scheme, the wireless communication interface 2012 may support another type of wireless communication scheme, such as a short-range wireless communication scheme, a near field communication scheme, and a wireless local area network (LAN) scheme. In this case, the wireless communication interface 2012 may include a BB processor 2013 and an RF circuit 2014 for each wireless communication scheme.

Each of the antenna switches 2015 switches a connection destination of the antenna 2016 among multiple circuits (for example, circuits for different wireless communication schemes) included in the wireless communication interface 2012.

Each of the antennas 2016 includes a single or multiple antenna elements (such as multiple antenna elements included in a MIMO antenna), and is used for the wireless communication interface 2012 to transmit and receive wireless signals. As shown in FIG. 10, the smartphone 2000 may include multiple antennas 2016. Although FIG. 10 shows an example in which the smartphone 2000 includes multiple antennas 2016, the smartphone 2000 may include a single antenna 2016.

In addition, the smartphone 2000 may include antenna(s) 2016 for each wireless communication scheme. In this case, the antenna switches 2015 may be omitted from the configuration of the smart phone 2000.

The processor 2001, the memory 2002, the storage device 2003, the external connection interface 2004, the camera device 2006, the sensor 2007, the microphone 2008, the input device 2009, the display device 2010, the speaker 2011, the wireless communication interface 2012, and the auxiliary controller 2019 are connected to each other via the bus 2017. The battery 2018 supplies power to each block of the smartphone 2000 shown in FIG. 10 via a feeder line. The feeder line is partially shown as a dashed line in FIG. 10. The auxiliary controller 2019 operates the minimum necessary functions of the smartphone 2000 in a sleep mode, for example.

In the smartphone 2000 shown in FIG. 10, at least part of the functions of the sound generation unit and the sound signal generation unit of the information processing apparatus 200 may be implemented by the processor 2001 or the auxiliary controller 2019. For example, the processor 2001 or the auxiliary controller 2019 may implement all or part of the functions of the units by executing instructions stored in the memory 2002 or the storage device 2003. Furthermore, the communication unit in the information processing apparatus 200 may be implemented via the wireless communication interface 2012 or optionally the antenna 2016. Furthermore, the storage unit in the information processing apparatus 200 may be implemented via the memory 2002 or the storage device 2003.

Second Application Example

Figure 11:
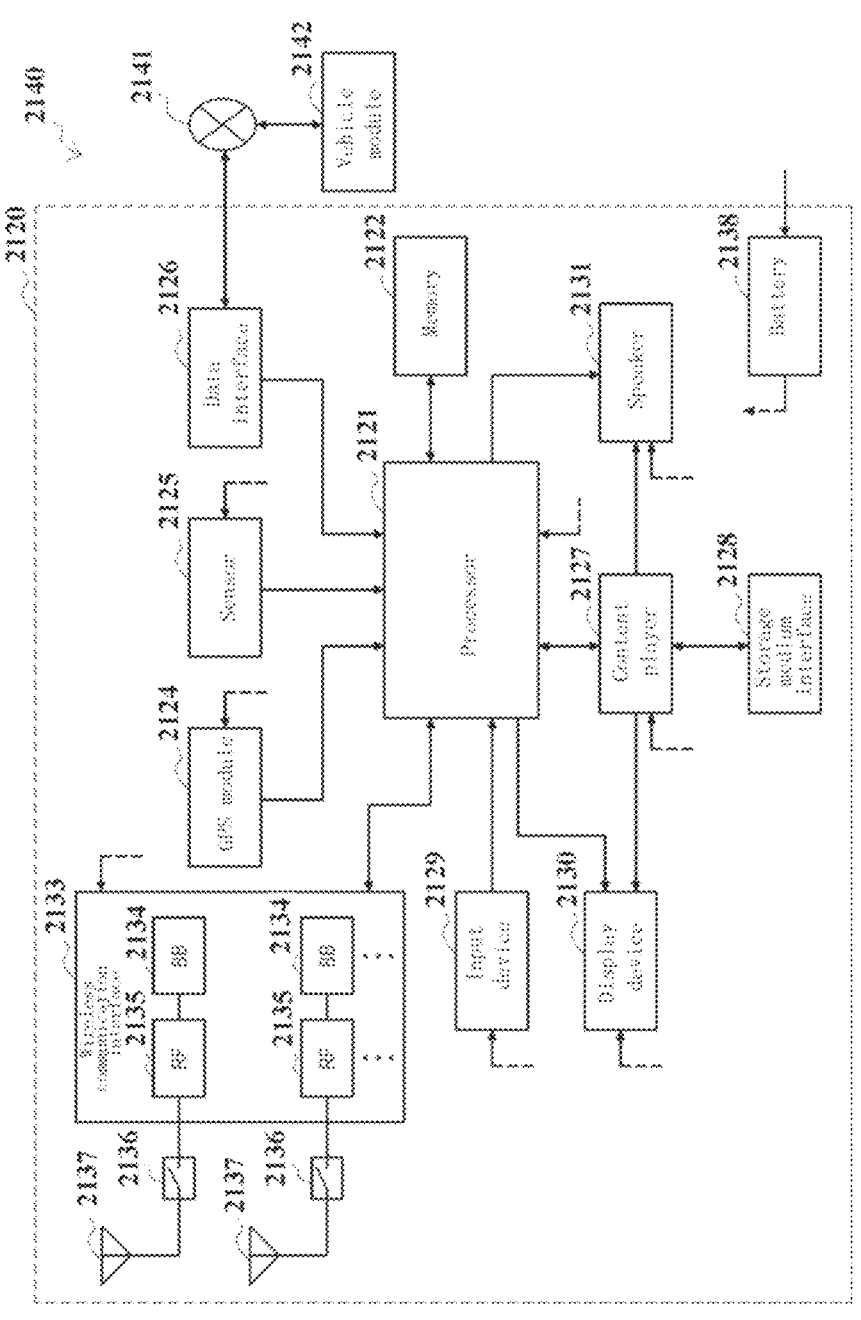
FIG. 11 is a block diagram showing an example of a schematic configuration of a car navigation device to which the technology of the present disclosure may be applied.

FIG. 11 is a block diagram showing an example of a schematic configuration of a vehicle navigation device 2120 to which the technology of the present disclosure may be applied. The vehicle navigation device 2120 includes a processor 2121, a memory 2122, a global positioning system (GPS) module 2124, a sensor 2125, a data interface 2126, a content player 2127, a storage medium interface 2128, an input device 2129, a display device 2130, a speaker 2131, a wireless communication interface 2133, one or more antenna switches 2136, one or more antennas 2137, and a battery 2138.

The processor 2121 may be, for example, a CPU or SoC, and controls the navigation function of the vehicle navigation device 2120 and other functions. The memory 2122 includes a RAM and a ROM, and stores data and programs executed by the processor 2121.

The GPS module 2124 measures a position (such as latitude, longitude, and altitude) of the vehicle navigation device 2120 based on GPS signals received from GPS satellites. The sensor 2125 may include a group of sensors, such as a gyroscope sensor, a geomagnetic sensor, and an air pressure sensor. The data interface 2126 is connected to, for example, a vehicle-mounted network 2141 via a terminal not shown, and acquires data (such as vehicle speed data) generated by the vehicle.

The content player 2127 reproduces content stored in a storage medium (such as CD and DVD) inserted into the storage medium interface 2128. The input device 2129 includes, for example, a touch sensor configured to detect a touch on a screen of the display device 2130, a button, or a switch, and receives an operation or information inputted from the user. The display device 2130 includes a screen such as an LCD or OLED display, and displays an image of a navigation function or reproduced content. The speaker 2131 outputs a sound of the navigation function or the reproduced content.

The wireless communication interface 2133 supports any cellular communication scheme (such as LTE and LTE-Advanced), and performs wireless communication. The wireless communication interface 2133 may generally include, for example, a BB processor 2134 and an RF circuit 2135. The BB processor 2134 may perform, for example, encoding/decoding, modulation/demodulation, and multiplexing/demultiplexing, and perform various types of signal processing for wireless communication. Further, the RF circuit 2135 may include, for example, a mixer, a filter, and an amplifier, and transmit and receive wireless signals via the antenna 2137. The wireless communication interface 2133 may also be a chip module on which the BB processor 2134 and the RF circuit 2135 are integrated. As shown in FIG. 11, the wireless communication interface 2133 may include multiple BB processors 2134 and multiple RF circuits 2135. Although FIG. 11 shows an example in which the wireless communication interface 2133 includes multiple BB processors 2134 and multiple RF circuits 2135, the wireless communication interface 2133 may include a single BB processor 2134 or a single RF circuit 2135.

In addition to the cellular communication scheme, the wireless communication interface 2133 may support another type of wireless communication scheme, such as a short-range wireless communication scheme, a near field communication scheme, or a wireless LAN scheme. In this case, the wireless communication interface 2133 may include a BB processor 2134 and an RF circuit 2135 for each wireless communication scheme.

Each of the antenna switches 2136 switches a connection destination of the antenna 2137 among multiple circuits, such as circuits for different wireless communication schemes, included in the wireless communication interface 2133.

Each of the antennas 2137 includes a single or multiple antenna elements (such as multiple antenna elements included in a MIMO antenna), and is used for the wireless communication interface 2133 to transmit and receive wireless signals. As shown in FIG. 11, the vehicle navigation device 2120 may include multiple antennas 2137. Although FIG. 11 shows an example in which the vehicle navigation device 2120 includes multiple antennas 2137, the vehicle navigation device 2120 may include a single antenna 2137.

In addition, the vehicle navigation device 2120 may include antenna(s) 2137 for each wireless communication scheme. In this case, the antenna switches 2136 may be omitted from the configuration of the vehicle navigation device 2120.

The battery 2138 supplies power to each block of the vehicle navigation device 2120 shown in FIG. 11 via a feeder line. The feeder line is partially shown as a dashed line in FIG. 11. The battery 2138 accumulates electric power supplied from the vehicle.

In the vehicle navigation device 2120 shown in FIG. 11, at least part of the functions of the sound generation unit and the sound signal generation unit of the information processing apparatus 200 described with reference to FIG. 2 may be implemented by the processor 2121. For example, the processor 2121 may implement all or part of the functions of the units by executing instructions stored in the memory 2122. Furthermore, the communication unit in the information processing apparatus 200 may be implemented via the wireless communication interface 2133 or optionally the antenna 2137. Furthermore, the storage unit in the information processing apparatus 200 may be implemented via the memory 2122.

The technology of the present disclosure may also be implemented as an in-vehicle system (or vehicle) 2140 including the vehicle navigation device 2120, a vehicle-mounted network 2141, and one or more blocks of vehicle modules 2142. The vehicle modules 2142 generate vehicle data (such as vehicle speed, engine speed, and failure information), and outputs the generated data to the vehicle-mounted network 2141.

Moreover, a program product storing machine-readable instruction codes is further provided according to an embodiment of the present disclosure. The instruction codes, when being read and executed by a machine, may implement the methods according to the embodiments of the present disclosure.

Accordingly, a storage medium for carrying the program product storing the machine-readable instruction codes is further included in the present disclosure. The storage medium includes, but is not limited to, a floppy disk, an optical disk, a magneto-optical disk, a storage card, a memory stick, and the like.

Figure 12:
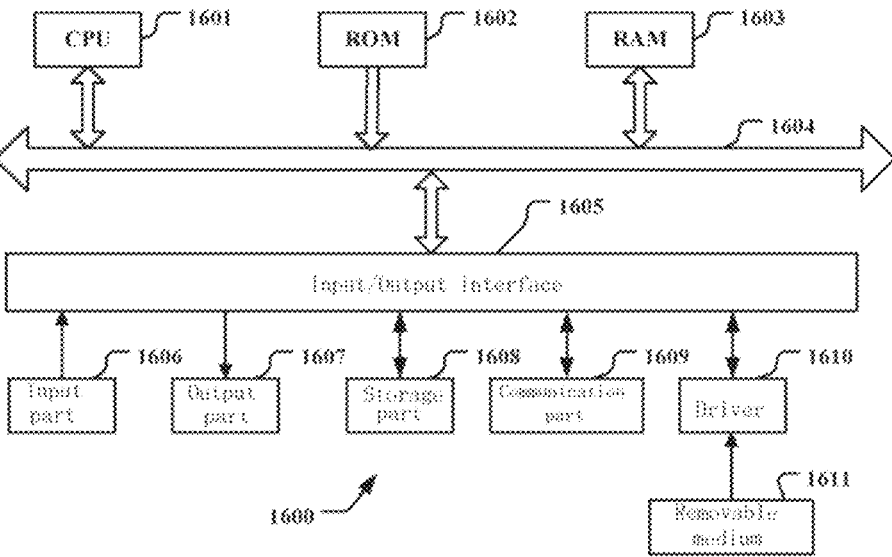
FIG. 12 is a block diagram of an exemplary structure of a general-purpose personal computer in which a method and/or apparatus and/or system according to an embodiment of the present disclosure may be implemented.

In a case of implementing the embodiments of the present disclosure in software or firmware, the program consisting of the software is mounted to a computer with a dedicated hardware structure (such as a general-purpose personal computer 1600 as shown in FIG. 12) from the storage medium or network. The computer, when mounted with various programs, performs various functions.

In FIG. 12, a central processing unit (CPU) 1601 executes various processing according to a program stored in a read-only memory (ROM) 1602 or a program loaded from a storage part 1608 to a random-access memory (RAM) 1603. In the RAM 1603, data required for the CPU 1601 to perform various processes or the like is also stored as necessary. The CPU 1601, the ROM 1602 and the RAM 1603 are connected to each other via a bus 1604. An input/output interface 1605 is also connected to the bus 1604.

The following components are connected to the input/output interface 1605: an input part 1606 (including a keyboard, a mouse, and the like), an output part 1607 (including a display, such as a cathode ray tube (CRT) and a liquid crystal display (LCD), a loudspeaker, and the like), a storage portion 1608 (including a hard disk, and the like), and a communication part 1609 (including a network interface card, such as a LAN card, and a modem). The communication part 1609 performs communication processing via a network, such as the Internet. A driver 1610 may also be connected to the input/output interface 1605 as needed. The removable medium 1611, such as a magnetic disk, an optical disk, a magnetic optical disk, a semiconductor memory, may be mounted to the driver 1610 as required, so that the computer program read therefrom is mounted to the storage part 1608 as required.

In a case of implementing the above processes in software, the program consisting of the software is mounted from a network, such as the Internet, or from a storage medium, such as the removable medium 1611.

Those skilled in the art should understood that, the storage medium is not limited to the removable medium 1611 as shown in FIG. 12 which stores a program and is distributed separately from the device so as to provide the program for the user. Examples of the removable medium 1611 includes a magnetic disk (including a soft disk (registered trademark)), an optical disk (including a compact disk read-only memory (CD-ROM) and a Digital Video Disk (DVD)), a magnetic optical disk (including a mini disk (MD) (registered trademark)), and a semiconductor memory. Alternatively, the storage medium may be the ROM 1602, the hard disk contained in the storage part 1608, or the like. The storage medium stores program and is distributed to the user along with an apparatus in which the storage medium is incorporated.

Preferred embodiments of the present disclosure are described above with reference to the drawings. However, the present disclosure is not limited to the above examples. Those skilled in the art may make various alternations and modifications within the scope of the appended claims. It should be understood that these alternations and modifications shall naturally fall within the technical scope of the present disclosure.

For example, units shown by a dotted line block in the functional block diagram shown in the drawings indicate that the functional units are optional in the corresponding device, and the optional functional units may be combined appropriately to achieve required functions.

For example, multiple functions implemented by one unit in the above embodiments may be implemented by separate apparatus. Alternatively, multiple functions implemented by multiple units in the above embodiments may be implemented by separate apparatus, respectively. In addition, one of the above functions may be implemented by multiple units. Such configurations are naturally included in the technical scope of the present disclosure.

In the specification, steps described in the flowchart include not only the processes performed chronologically as the described sequence, but also the processes performed in parallel or individually rather than chronologically. Furthermore, the steps performed chronologically may be performed in other order appropriately.

Furthermore, the present disclosure may have configurations as described below.

1. An information processing apparatus, comprising processing circuitry, configured to obtain a sound field in a virtual space, by using a sound field synthesis model, based on sound source information about a sound source in a real space and virtual space information indicating an object present in the virtual space, wherein the sound field synthesis model is pre-obtained through machine learning by using a sound field in a virtual space obtained from high-precision calculation as learning data.

2. The information processing apparatus according to configuration 1, wherein the processing circuitry is further configured to: determine the sound source in the real space through blind sound source detection based on sound signals obtained from a plurality of sound collection apparatuses disposed at different positions in the real space, to obtain the sound source information.

3. The information processing apparatus according to configuration 1, wherein the sound field synthesis model is a model based on a convolutional neural network.

4. The information processing apparatus according to configuration 3, wherein the processing circuitry is further configured to: generate an ideal sound field map representing an ideal sound field in the virtual space without an object, based on the sound source information about the sound source in the real space.

5. The information processing apparatus according to configuration 4, wherein the processing circuitry is further configured to: generate a spatial structure map representing a spatial structure of the virtual space based on the virtual space information indicating a position and an attribute of the object in the virtual space.

6. The information processing apparatus according to configuration 5, wherein the processing circuitry is further configured to: input the ideal sound field map and the spatial structure map with a same resolution into the sound field synthesis model to obtain the sound field in the virtual space outputted from the sound field synthesis model.

7. The information processing apparatus according to configuration 1, wherein the processing circuitry is further configured to: perform high-precision calculation based on information about a training sound source in the real space and a spatial structure of a training virtual space, to obtain a sound field in the training virtual space as the learning data.

8. The information processing apparatus according to configuration 1, wherein the processing circuitry is further configured to:

generate a sound signal suitable for a user based on a position of the user and the sound field in the virtual space.

9. The information processing apparatus according to configuration 8, wherein the processing circuitry is further configured to:

extract an auditory feature of the user based on a physiological attribute of the user by using an auditory feature extraction model;

select, based on the extracted auditory feature, at least one mixing modes from a database which stores auditory features and mixing modes in association with each other;

determine a mixing mode for the user based on the selected mixing mode; and perform mixing on the sound signal in the determined mode to generate a sound signal to be outputted to the user.

10. The information processing apparatus according to configuration 9, wherein the physiological attribute of the user comprises one or more of age, gender, and an ear morphological feature of the user.

11. The information processing apparatus according to configuration 9, wherein the processing circuitry is further configured to: obtain the auditory feature extraction model through metric learning by using pre-obtained historical data of physiological attributes and mixing modes in association with each other.

12. An information processing method, comprising:

obtaining a sound field in a virtual space, by using a sound field synthesis model, based on sound source information about a sound source in a real space and virtual space information indicating an object present in the virtual space, wherein the sound field synthesis model is pre-obtained through machine learning by using a sound field in a virtual space obtained from high-precision calculation as learning data.

13. The information processing method according to configuration 12, further comprising: determining the sound source in the real space through blind sound source detection based on sound signals obtained from a plurality of sound collection apparatuses disposed at different positions in the real space, to obtain the sound source information.

14. The information processing method according to configuration 12, wherein the sound field synthesis model is a model based on a convolutional neural network.

15. The information processing method according to configuration 14, wherein an ideal sound field map representing an ideal sound field in the virtual space without an object is generated based on the sound source information about the sound source in the real space.

16. The information processing method according to configuration 15, wherein a spatial structure map representing a spatial structure of the virtual space is generated based on the virtual space information indicating a position and an attribute of the object in the virtual space.

17. The information processing method according to configuration 16, wherein the ideal sound field map and the spatial structure map with a same resolution are inputted into the sound field synthesis model to obtain the sound field in the virtual space outputted from the sound field synthesis model.

18. The information processing method according to configuration 12, wherein high-precision calculation is performed based on information about a training sound source in the real space and a spatial structure of a training virtual space, to obtain a sound field in the training virtual space as the learning data.

19. The information processing method according to configuration 12, further comprising:

generating a sound signal suitable for a user based on a position of the user and the sound field in the virtual space.

20. The information processing method according to configuration 19, further comprising:

extracting an auditory feature of the user based on a physiological attribute of the user by using an auditory feature extraction model;

selecting, based on the extracted auditory feature, at least one mixing modes from a database which stores auditory features and mixing modes in association with each other;

determining a mixing mode for the user based on the selected mixing mode; and performing mixing on the sound signal in the determined mode to generate a sound signal to be outputted to the user.

21. The information processing method according to configuration 20, wherein the physiological attribute of the user comprises one or more of age, gender, and an ear morphological feature of the user.

22. The information processing method according to configuration 20, wherein the auditory feature extraction model is obtained through metric learning by using pre-obtained historical data of physiological attributes and mixing modes in association with each other.

23. A non-transitory computer-readable storage medium storing executable instructions, wherein the executable instructions, when executed by a processor, cause the processor to perform the information processing method according to any one of configurations 12 to 22.

Although the embodiments of the present disclosure are described in detail above with reference to the accompanying drawings, it should be understood that the embodiments are only for illustrating the present disclosure and do not constitute a limitation of the present disclosure. For those skilled in the art, various modifications and changes can be made to the embodiments without departing from the spirit and scope of the present disclosure. Therefore, the scope of the present disclosure is limited by only the appended claims and equivalents thereof.

The invention claimed is:

1. An information processing apparatus, comprising processing circuitry, configured to obtain a sound field in a virtual space, by using a sound field synthesis model, based on sound source information about a sound source in a real space and virtual space information indicating an object present in the virtual space, wherein the sound field synthesis model is pre-obtained through machine learning by using a sound field in a virtual space obtained from high-precision calculation as learning data, wherein the sound field synthesis model is a model based on a convolutional neural network, and the processing circuitry is further configured to generate an ideal sound field map representing an ideal sound field in the virtual space without an object, based on the sound source information about the sound source in the real space.

2. The information processing apparatus according to claim 1, wherein the processing circuitry is further configured to: determine the sound source in the real space through blind sound source detection based on sound signals obtained from a plurality of sound collection apparatuses disposed at different positions in the real space, to obtain the sound source information.

3. The information processing apparatus according to claim 1, wherein the processing circuitry is further configured to: generate a spatial structure map representing a spatial structure of the virtual space based on the virtual space information indicating a position and an attribute of the object in the virtual space.

4. The information processing apparatus according to claim 3, wherein the processing circuitry is further configured to: input the ideal sound field map and the spatial structure map with a same resolution into the sound field synthesis model to obtain the sound field in the virtual space outputted from the sound field synthesis model.

5. The information processing apparatus according to claim 1, wherein the processing circuitry is further configured to: perform high-precision calculation based on information about a training sound source in the real space and a spatial structure of a training virtual space, to obtain a sound field in the training virtual space as the learning data.

6. The information processing apparatus according to claim 1, wherein the processing circuitry is further configured to:

generate a sound signal suitable for a user based on a position of the user and the sound field in the virtual space.

7. The information processing apparatus according to claim 6, wherein the processing circuitry is further configured to:

extract an auditory feature of the user based on a physiological attribute of the user by using an auditory feature extraction model;

select, based on the extracted auditory feature, at least one mixing modes from a database which stores auditory features and mixing modes in association with each other;

determine a mixing mode for the user based on the selected mixing mode; and perform mixing on the sound signal in the determined mode to generate a sound signal to be outputted to the user.

8. The information processing apparatus according to claim 7, wherein the physiological attribute of the user comprises one or more of age, gender, and an ear morphological feature of the user.

9. The information processing apparatus according to claim 7, wherein the processing circuitry is further configured to: obtain the auditory feature extraction model through metric learning by using pre-obtained historical data of physiological attributes and mixing modes in association with each other.

10. An information processing method, comprising:

obtaining a sound field in a virtual space, by using a sound field synthesis model, based on sound source information about a sound source in a real space and virtual space information indicating an object present in the virtual space, wherein the sound field synthesis model is pre-obtained through machine learning by using a sound field in a virtual space obtained from high-precision calculation as learning data, wherein the sound field synthesis model is a model based on a convolutional neural network, and an ideal sound field map representing an ideal sound field in the virtual space without an object is generated based on the sound source information about the sound source in the real space.

11. The information processing method according to claim 10, further comprising: determining the sound source in the real space through blind sound source detection based on sound signals obtained from a plurality of sound collection apparatuses disposed at different positions in the real space, to obtain the sound source information.

12. The information processing method according to claim 11, wherein a spatial structure map representing a spatial structure of the virtual space is generated based on the virtual space information indicating a position and an attribute of the object in the virtual space.

13. The information processing method according to claim 12, wherein the ideal sound field map and the spatial structure map with a same resolution are inputted into the sound field synthesis model to obtain the sound field in the virtual space outputted from the sound field synthesis model.

14. The information processing method according to claim 10, wherein high-precision calculation is performed based on information about a training sound source in the real space and a spatial structure of a training virtual space, to obtain a sound field in the training virtual space as the learning data.

15. The information processing method according to claim 10, further comprising:

generating a sound signal suitable for a user based on a position of the user and the sound field in the virtual space.

16. A non-transitory computer-readable storage medium storing executable instructions, wherein the executable instructions, when executed by a processor, cause the processor to perform the information processing method according to claim 10.

* * * * *